(12) United States Patent
Yoo et al.

(10) Patent No.: US 8,049,014 B2
(45) Date of Patent: Nov. 1, 2011

(54) AMINOQUINOLINE DERIVATIVES, PREPARATION METHOD THEREOF AND PHARMACEUTICAL COMPOSITION COMPRISING THE SAME

(75) Inventors: Kyung-Ho Yoo, Seoul (KR); Dong-Jin Kim, Seoul (KR); Bong-Soo Nam, Busan (KR); Chang-Hyun Oh, Seoul (KR); So-Ha Lee, Seoul (KR); Seung-Joo Cho, Seoul (KR); Tae-Bo Sim, Daegu (KR); Jung-Mi Hah, Seoul (KR)

(73) Assignee: Korea Institute of Science and Technology (KR)

( * ) Notice: Subject to any disclaimer, the term of this patent is extended or adjusted under 35 U.S.C. 154(b) by 359 days.

(21) Appl. No.: 12/468,292

(22) Filed: May 19, 2009

(65) Prior Publication Data

US 2010/0249182 A1    Sep. 30, 2010

(30) Foreign Application Priority Data

Mar. 25, 2009  (KR) ........................ 10-2009-0025560

(51) Int. Cl.
C07D 215/38   (2006.01)
A61K 31/04    (2006.01)

(52) U.S. Cl. ........................ 546/153; 514/312
(58) Field of Classification Search ............... 546/153; 514/312
See application file for complete search history.

(56) References Cited

U.S. PATENT DOCUMENTS

| 6,143,764 | A   | 11/2000 | Kubo et al. |
| 6,384,051 | B1* | 5/2002  | Frost et al. ............... 514/313 |
| 7,425,564 | B2  | 9/2008  | Fujiwara et al. ........... 514/312 |

FOREIGN PATENT DOCUMENTS

| WO | WO 96/09294   | 3/1996  |
| WO | WO 2006/108059 | 10/2006 |
| WO | WO 2008/048375 | 4/2008  |

OTHER PUBLICATIONS

Office Action issued by the Korean Patent Office on Feb. 1, 2011 in connection with corresponding Korean Patent Application No. 10-2009-00025560.

Scott M. Wilhelm et al., "Bay 43-9006 Exhibits Broad Spectrum Oral Antitumor Activity and Targets the RAF/MEK/ERK Pathway and Receptor Tyrosine Kinases Involved in Tumor Progression and Angiogenesis," Cancer Research 64, 7099-7109, Oct. 1, 2004.

\* cited by examiner

*Primary Examiner* — D M Seaman
(74) *Attorney, Agent, or Firm* — Ostrolenk Faber LLP

(57) ABSTRACT

Provided are a novel aminoquinoline compound represented by Formula 1 or a pharmaceutically acceptable salt thereof, preparation method thereof, and a pharmaceutical composition for preventing or treating cutaneous cancer, comprising the aminoquinoline compound or pharmaceutically acceptable salt thereof. Since the compound of Formula 1 exhibits excellent anti-proliferative effect on melanoma tumor cells, it is useful for preventing or treating cutaneous cancer.

Formula 1:

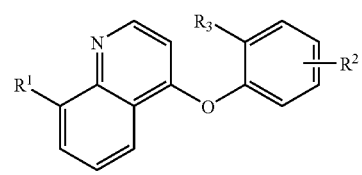

wherein $R^1$, $R^2$, and $R^3$ are defined in the specification.

17 Claims, No Drawings

AMINOQUINOLINE DERIVATIVES, PREPARATION METHOD THEREOF AND PHARMACEUTICAL COMPOSITION COMPRISING THE SAME

BACKGROUND OF THE INVENTION

1. Field of the Invention

The present invention relates to an aminoquinoline derivative or a pharmaceutically acceptable salt thereof which exhibits excellent anti-proliferative effect on melanoma tumor cells, a preparation method thereof, and a pharmaceutical composition for preventing or treating cutaneous cancer, comprising the aminoquinoline derivative as an effective ingredient.

2. Description of the Related Art

Cutaneous cancer generally refers to all kinds of cancers produced in skin, representative of which are basal cell carcinoma, squamous epithelial carcinoma, melanoma, and the like. Melanoma, which is a cancer generally produced in skin, is produced in any part where melanin cells exist; however, it most frequently appears in skin. In general, melanoma is frequently produced for the whites and rare for the yellow or black race, but if one does work in the fields or open air for a long time, there is a high risk of being attacked by the disease. The cause of melanoma has not been precisely revealed yet, and it has been simply known as a tumor developed as nevus cells or melanocytes which are skin cells producing melanic pigment become malignant. A certain family group shows a genetic predisposition. A malignant melanoma usually does not give any subjective symptoms such as pruritus, pain or the like, and appears as yellowish brown or black-colored spots or tubers; therefore, it is difficult to be found by self diagnosis.

Since melanoma is a malignant cutaneous tumor with a gloomy prognosis compared with other cutaneous cancers, its early diagnose and treatment are very critical. Its treatment includes excision of lesion through a surgical operation. However, if the excision treatment is imperfect or impossible, a chemotherapy, a laser therapy, a radiotherapy or the like is performed, but it has been known that there is no secure curative means except for a surgical operation.

An early stage of melanoma may be cured through a surgical operation, while melanoma cells spread to other organs are resistant to all existing therapeutic agents. Therapeutic agents developed until now have characteristics of symptom alleviators accompanying various side effects, not a therapeutic agent for a fundamental treatment. In a chemotherapy for developed melanoma, dacarbazine (DTIC) is the sole FDA-approved medical product, but it merely offers less than 5% of complete recovery rate (See Anderson, C. M et al., Oncol. 1995, 9, 1149; Serrone, L. et al., J. Exp. Clin. Cancer Res. 2000, 19, 21). The metastatic melanoma still has resistance to triazine derivatives such as DTIC, temozolomide, etc. (See Chang, J. et al., Eur. J. Cancer 1994, A, 2093; Fletcher, W. S. et al., Am. J. Clin. Oncol. 1993, 16, 359), nitrosourea derivatives such as carmustine (BCNU), lomustine (CCNU), fotemustine, etc. (See Madajewicz, S. et al., Cancer 1981, 47, 653; and Avril, M. F. et al., J. Clin. Oncol. 2004, 22, 1118), a combination therapy of cisplatin with etoposide (See Franciosi, V. et al., Cancer 1999, 85, 1599; and Mandara, M. et al., Expert Rev. Anticancer Ther. 2006, 6, 121), and the like. The period of survival in the developed metastatic melanoma is below one year on average, and a five year survival rate is less than 15% (See Carlson, J. A. et al., J. Am. Acad. Dermatol. 2005, 52, 743; Atallah, E. et al., Curr. Treat. Options Oncol. 2005, 6, 185; and Gogas, H. J. et al., Cancer 2007, 109, 455).

Therefore, the development of a compound having good anti-proliferative effects on melanoma tumor cells while causing fewer side effects, so as to be useful for preventing or treating cutaneous cancer is of urgency.

SUMMARY OF THE INVENTION

Therefore, in order to address the above matters, the various features described herein have been conceived.

An object of the prevent invention is to provide a novel aminoquinoline derivative or a pharmaceutically acceptable salt thereof.

Another object of the present invention is to provide a preparation method of the aminoquinoline derivative or pharmaceutically acceptable salt thereof.

Still another object of the present invention is to provide a pharmaceutical composition for preventing or treating cutaneous cancer, comprising the aminoquinoline derivative or pharmaceutically acceptable salt thereof as an effective ingredient.

DISCLOSURE OF THE INVENTION

The inventors of the present invention has completed the invention by discovering that an aminoquinoline derivative, a small molecule which has a little possibility of causing side effects and exhibits excellent anti-proliferative effect on melanoma tumor cells, so as to be useful for preventing or treating cutaneous cancer.

The above objects of the present invention are achieved by providing a novel aminoquinoline compound represented by the following Formula 1 or a pharmaceutically acceptable salt thereof, and preparation method thereof:

Formula 1:

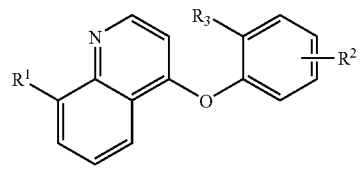

wherein
$R^1$ is $NH_2$ or $NHCOR^4$;
$R^2$ is $NHCONHR^5$ or $NHCOR^5$;
$R^3$ is H or $C_1$-$C_6$ alkyl;
$R^4$ is $C_1$-$C_6$ alkyl or $C_6$-$C_{10}$ aryl;
$R^5$ is $C_6$-$C_{10}$ aryl or $C_3$-$C_6$ heteroaryl which is unsubstituted or substituted with one or more substituents selected from the group consisting of $C_1$-$C_6$ alkyl; one or more halogen atoms selected from the group consisting of fluorine, chlorine, bromine and iodine; $C_1$-$C_6$ alkyl substituted with one or more halogen atoms selected from the group consisting of fluorine, chlorine, bromine and iodine; nitro; substituted or unsubstituted piperidinyl; substituted or unsubstituted imidazolyl; substituted or unsubstituted isoxazolyl; and substituted or unsubstituted morpholinyl, wherein the substituent on the piperidinyl, imidazolyl, isoxazolyl or morpholinyl is hydroxyl or $C_1$-$C_6$ alkyl.

The other objects of the present invention are achieved by providing a pharmaceutical composition for preventing or treating cutaneous cancer, comprising the aminoquinoline compound of Formula 1 or pharmaceutically acceptable salt thereof as an effective ingredient, and an agent for inhibiting proliferation of melanoma tumor cells.

DETAILED DESCRIPTION OF THE INVENTION

The present invention relates to an aminoquinoline compound represented by Formula 1 below, or a pharmaceutically acceptable salt thereof:

Formula 1:

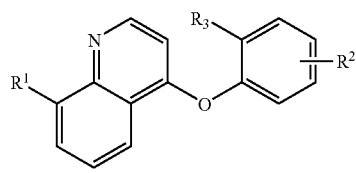

wherein
$R^1$ is $NH_2$ or $NHCOR^4$;
$R^2$ is $NHCONHR^5$ or $NHCOR^5$;
$R^3$ is H or $C_1$-$C_6$ alkyl;
$R^4$ is $C_1$-$C_6$ alkyl or $C_6$-$C_{10}$ aryl;
$R^5$ is $C_6$-$C_{10}$ aryl or $C_3$-$C_6$ heteroaryl which is unsubstituted or substituted with one or more substituents selected from the group consisting of $C_1$-$C_6$ alkyl; one or more halogen atoms selected from the group consisting of fluorine, chlorine, bromine and iodine; $C_1$-$C_6$ alkyl substituted with one or more halogen atoms selected from the group consisting of fluorine, chlorine, bromine and iodine; nitro; substituted or unsubstituted piperidinyl; substituted or unsubstituted imidazolyl; substituted or unsubstituted isoxazolyl; and substituted or unsubstituted morpholinyl, wherein the substituent on the piperidinyl, imidazolyl, isoxazolyl or morpholinyl is hydroxyl or $C_1$-$C_6$ alkyl.

In Formula 1, if $R^1$ is $NHCOR^4$ group, $R^4$ is most preferably methyl or phenyl.

It is preferred that in Formula 1, $R^5$ is unsubstituted phenyl; or phenyl substituted with at least one substituent selected from the group consisting of halogen; $C_1$-$C_6$ alkyl which is substituted with one or more halogen; nitro; hydroxyl piperidinyl; imidazolyl which is unsubstituted or substituted with $C_1$-$C_6$ alkyl; and isoxazolyl which is unsubstituted or substituted with $C_1$-$C_6$ alkyl, wherein the halogen is selected from the group consisting of fluorine, chlorine, bromine and iodine.

The preferred examples of the aminoquinoline compound of Formula 1 according to the present invention are as follows:

(1a) 1-[4-(8-aminoquinolin-4-yloxy)phenyl]-3-(4-chloro-3-trifluoromethyl-phenyl)urea;
(1b) N-[4-(8-aminoquinolin-4-yloxy)phenyl]-4-chloro-3-trifluoromethylbenzamide;
(1c) 1-[4-(8-acetylaminoquinolin-4-yloxy)phenyl]-3-(4-chloro-3-trifluoro-methylphenyl)urea;
(1d) N-[4-(8-acetylaminoquinolin-4-yloxy)phenyl]-4-chloro-3-trifluoromethylbenzamide;
(1e) N-[4-(8-benzoylaminoquinolin-4-yloxy)phenyl]-4-chloro-3-trifluoromethylbenzamide;
(1f) 1-[3-(8-aminoquinolin-4-yloxy)phenyl]-3-(4-chloro-3-trifluoromethyl-phenyl)urea;
(1g) N-[3-(8-aminoquinolin-4-yloxy)phenyl]-4-chloro-3-trifluoromethylbenzamide;
(1h) 1-[3-(8-acetylaminoquinolin-4-yloxy)phenyl]-3-(4-chloro-3-trifluoro-methylphenyl)urea;
(1i) N-[3-(8-acetylaminoquinolin-4-yloxy)phenyl]-4-chloro-3-trifluoromethylbenzamide;
(1j) N-[3-(8-benzoylaminoquinolin-4-yloxy)phenyl]-4-chloro-3-trifluoromethylbenzamide;
(1k) N-[3-(8-acetylaminoquinolin-4-yloxy)-4-methylphenyl]-4-chloro-3-trifluoromethylbenzamide;
(1l) N-[3-(8-acetylaminoquinolin-4-yloxy)-4-methylphenyl]-3-trifluoromethylbenzamide;
(1m) N-[3-(8-acetylaminoquinolin-4-yloxy)-4-methylphenyl]-3,5-bistrifluoromethylbenzamide;
(1n) N-[3-(8-acetylaminoquinolin-4-yloxy)-4-methylphenyl]-4-nitro-3-trifluoromethylbenzamide;
(1o) N-[3-(8-acetylaminoquinolin-4-yloxy)-4-methylphenyl]-3-(4-hydroxypiperidin-1-yl)-5-trifluoromethylbenzamide;
(1p) N-[3-(8-acetylaminoquinolin-4-yloxy)-4-methylphenyl]-3-(4-methylimidazol-1-yl)-5-trifluoromethylbenzamide;
(1q) N-[3-(8-acetylaminoquinolin-4-yloxy)-4-methylphenyl]-2-chlorobenzamide;
(1r) N-[3-(8-acetylaminoquinolin-4-yloxy)-4-methylphenyl]-5-methylisoxazole-3-carboxylic acid amide; and
(1s) N-[3-(8-benzoylaminoquinolin-4-yloxy)-4-methylphenyl]-4-chloro-3-trifluoromethylbenzamide.

The aminoquinoline compound according to the present invention represented by Formula 1 may be used in the form of a pharmaceutically acceptable salt derived with an inorganic or organic acid, and preferred salts may include, but not limited thereto, salts with hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, toluenesulfonic acid, or the like.

The present invention also relates to a preparation method of the aminoquinoline compound represented by Formula 1 or a pharmaceutically acceptable salt thereof.

Hereinafter, specific examples of the preparation method of the aminoquinoline compound represented by Formula 1 will now be described with reference to Reaction Schemes 1 and 2.

Preparation Method 1

As illustrated in Reaction Scheme 1 below, a preparation method of the compound of Formula 1 in which $R^3$ is hydrogen, or a pharmaceutically acceptable salt thereof, comprises:

(1) nitration of a compound of Formula 2 below so as to obtain a compound of Formula 3 below;

Formula 2:

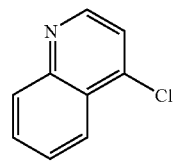

Formula 3:

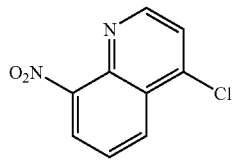

(2) substitution reaction of the compound of Formula 3 obtained in step (1) with an aminophenol so as to obtain a compound of Formula 4 below;

Formula 4:

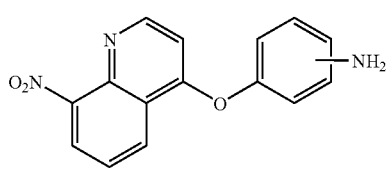

(3) coupling of the compound of Formula 4 obtained in step (2) with an isocyanate of a general formula R⁵—NCO or a carboxylic acid of a general formula R⁵—CO₂H, so as to obtain a compound of Formula 5 below;

Formula 5:

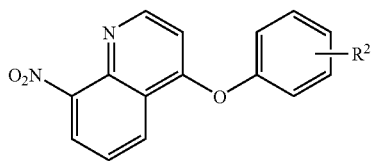

(4) reduction of the compound of Formula 5 obtained in step (3) so as to obtain a compound of Formula 6 below; and Formula 6:

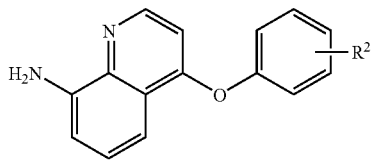

(5) amidation of the compound of Formula 6 obtained in step (4) with a carboxylic acid of a general formula R⁴—CO₂H so as to obtain the compound of Formula 1 in which R³ is hydrogen.

Reaction Scheme 1:

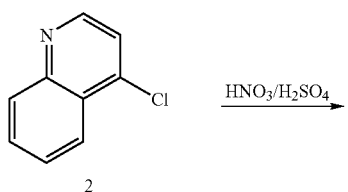

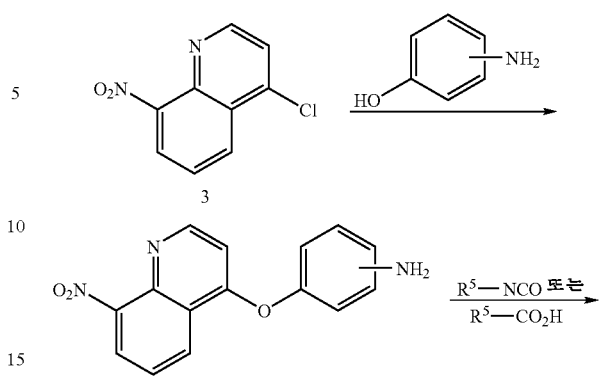

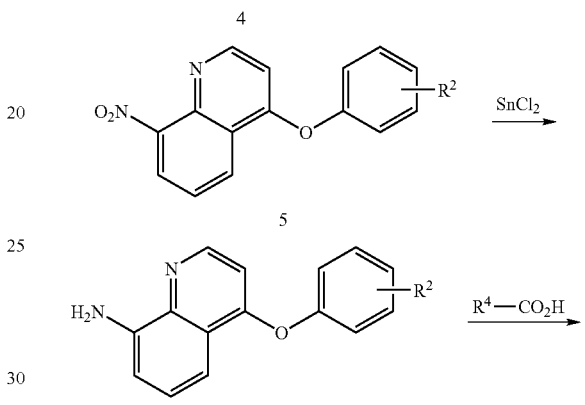

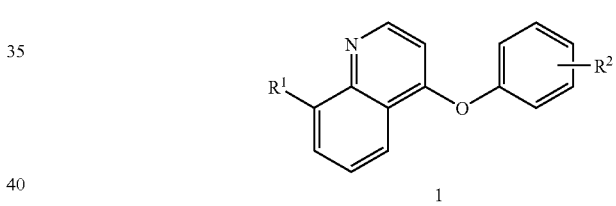

In the above Formulae 2 to 6, and Reaction Scheme 1, R¹, R², R⁴ and R⁵ are the same as those defined with respect to Formula 1.

Preparation Method 2

As illustrated in Reaction Scheme 2 below, a preparation method of the compound of Formula 1 in which R³ is an alkyl group (R³ is a methyl group in Reaction Scheme 2), or a pharmaceutically acceptable salt thereof, comprises:

(1) substitution reaction of the above compound of Formula 3 with a protected aminophenol so as to obtain a compound of Formula 7 below;

Formula 7:

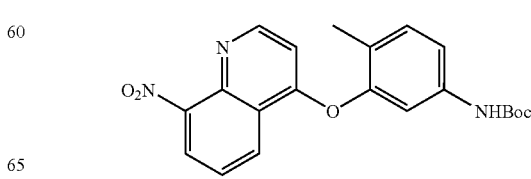

(2) reduction of the compound of Formula 7 obtained in step (1) so as to obtain a compound of Formula 8 below;

Formula 8:

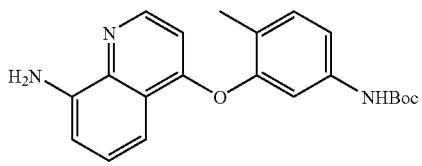

(3) amidation of the compound of Formula 8 obtained in step (2) with a carboxylic acid of a general formula $R^4$—$CO_2H$ so as to obtain a compound of Formula 9 below;

Formula 9:

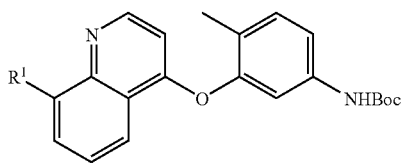

(4) deprotection of the compound of Formula 9 obtained in step (3) so as to obtain a compound of Formula 10 below; and Formula 10:

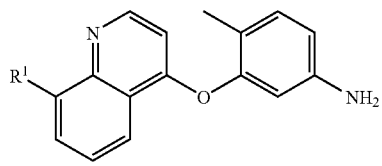

(5) coupling of the compound of Formula 10 obtained in step (4) with an isocyanate of a general formula $R^5$—NCO or a carboxylic acid of a general formula $R^5$—$CO_2H$, so as to obtain the compound of Formula 1 in which $R^3$ is an alkyl.

Reaction Scheme 2:

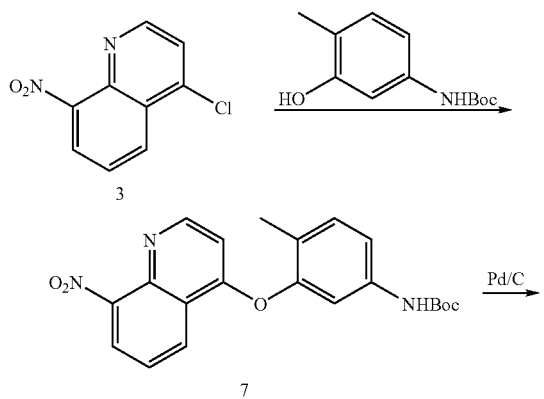

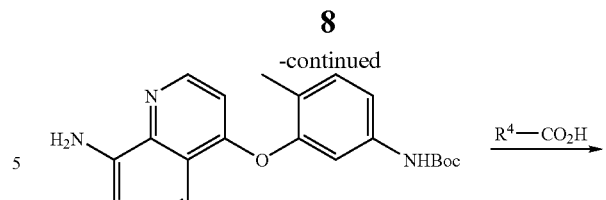

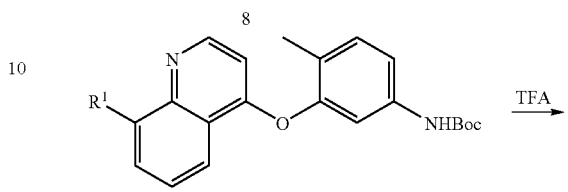

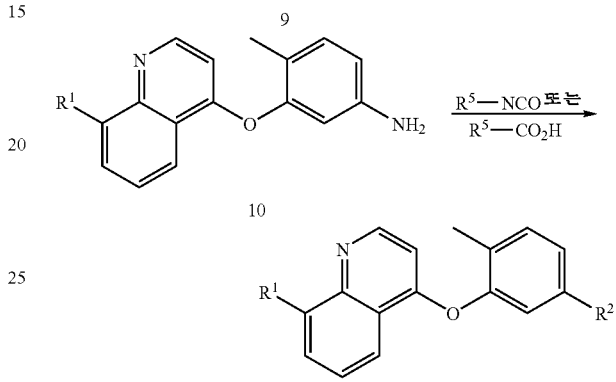

In Formulae 7 to 10, and Reaction Scheme 2, $R^1$, $R^2$, $R^4$ and $R^5$ are the same as those defined with respect to Formula 1.

The pharmaceutically acceptable salt of the compound represented by Formula 1 may be obtained by reacting the compound of Formula 1 with an inorganic or organic acid as mentioned above according to a conventional method known to a person skilled in the art.

The preferred example of the carboxylic acid of the general formula $R^4$—$CO_2H$ which is used for preparing the compound of Formula 1 of the present invention includes, but not limited thereto, a compound selected from the group consisting of the structures below:

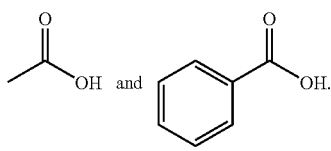

The preferred example of the isocyanate of the general formula $R^5$—NCO or the carboxylic acid of the general formula $R^5$—$CO_2H$ which is used for preparing the compound of Formula 1 of the present invention includes, but not limited thereto, a compound selected from the group consisting of the structures below:

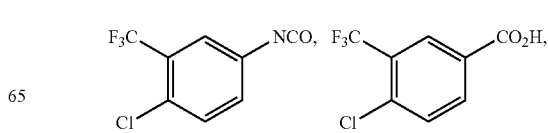

-continued

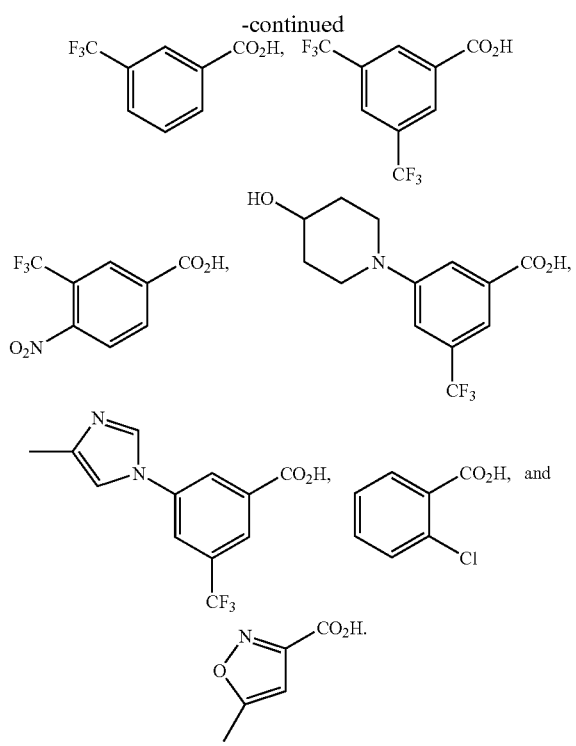

Since the compound of Formula 1 or pharmaceutically acceptable salt thereof can inhibit proliferation of melanoma tumor cells, they are suitable for preventing or treating cutaneous cancer.

Thus, the present invention relates to a pharmaceutical composition for preventing or treating cutaneous cancer, comprising a compound represented by Formula 1 or a pharmaceutically acceptable salt thereof as an effective ingredient.

The cutaneous cancer on which the compound of the present invention can exhibits treatment effects includes diseases related to all kinds of cancers produced in skin, for example, basal cell carcinoma, squamous epithelial carcinoma, and the like, as well as melanoma.

The pharmaceutical composition according to the present invention may comprise a compound of Formula 1 or a pharmaceutically acceptable salt thereof, as an effective ingredient, in an amount of 0.5 to 10% by weight, preferably, 0.5 to 5% by weight of the total weight of the composition.

The pharmaceutical composition according to the present invention may be prepared in various formulations for oral or parenteral administration. The formulation for oral administration may be in the form of tablet, pill, hard or soft capsule, liquid, suspension, emulsion, syrup, granule, and the like. The formulation for oral administration may comprise one or more diluents (e.g., lactose, dextrose, sucrose, mannitol, sorbitol, cellulose, and/or glycine), one or more lubricants (e.g., silica, talc, stearic acid and magnesium or calcium salt thereof, and/or polyethyleneglycol), in addition to the effective ingredient. Tablet may comprise a bonding agent such as magnesium aluminum silicate, starch paste, gelatine, tragacanth, methylcellulose, sodium carboxylmethylcelluose and/or polyvinylpyrolidine, and may optionally comprise a disintegrant such as starch, agar, alginic acid or its sodium salt; an effervescent mixture and/or an absorbent; a coloring agent; a flavoring agent; or a sweetener. A typical example of the formulation for parenteral administration is a formulation for an injection, preferably, an isotonic aqueous solution or suspension.

The composition may be sterilized and/or further comprise additives such as an anticeptic, a stabilizer, a hydrating agent or an emulsifying accelerator, a salt for adjusting osmotic pressures and/or a buffer. The composition may further comprise any therapeutically useful substances, and it may be formulated in accordance with a conventional method including mixing, granulation and coating.

The compound of Formula 1 or a pharmaceutically acceptable salt thereof may be orally or parenterally administered to mammals including human in an amount of 0.001 to 100 mg/kg body weight, preferably, 0.01 to 35 mg/kg body weight per day, at one time or divided.

EXAMPLES

The present invention will be described in more detail by the following examples. However, the following examples are merely illustrative, and not to limit the scope of the present invention.

Example 1

Preparation of 1-[4-(8-aminoquinolin-4-yloxy)phenyl]-3-(4-chloro-3-trifluoromethylphenyl)urea (Compound 1a)

Step (1): Preparation of 4-chloro-8-nitroquinoline (Compound of Formula 3)

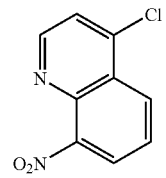

4-Chloroquinoline (5 g, 31 mmol) was dissolved in sulfuric acid (23 mL, 0.42 mol), to which nitric acid (4.5 mL, 0.11 mol) was slowly added dropwise, which was then stirred at room temperature for four hours. When the reaction was completed, the resultant was cooled to 0° C., and neutralized with 1M ammonium hydroxide. The generated solid was dissolved in ethyl acetate, dried with anhydrous sodium sulfate, and then filtered. The solvent was removed by vacuum distillation, and the residue was purified by a column chromatography (ethyl acetate/n-hexane=⅓) to obtain 3.55 g of the desired compound as a white solid (yield 55.7%).

$^1$H NMR (400 MHz, CDCl$_3$): δ 7.59 (d, J=6.76 Hz, 1H), 7.74 (t, J=8.02 Hz, 1H), 8.08 (d, J=7.33 Hz, 1H), 8.47 (d, J=8.44 Hz, 1H), 8.93 (d, J=4.59 Hz, 1H).

$^{13}$C NMR (75 MHz, CDCl$_3$): δ 122.94, 124.33, 126.34, 127.41, 128.19, 140.81, 143.23, 148.96, 152.00.

Step (2): Preparation of 4-(8-nitroquinolin-4-yloxy)phenylamine (Compound of Formula 4)

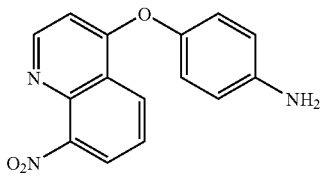

4-Chloro-8-nitroquinoline (176 mg, 0.85 mmol) and 4-aminophenol (93 mg, 0.85 mmol) were dissolved in dimethylformamide, and to which 1.0 M potassium tert-butoxide (0.95 mL) in tetrahydrofuran was slowly added dropwise at room temperature, which was then heated and stirred at 110° C. for seven hours. When the reaction was completed, the resultant was extracted with ethyl acetate and aqueous sodium chloride, and the combined organic layers were dried with anhydrous sodium sulfate, and then filtered. The solvent was removed by vacuum distillation, and the residue was purified by a column chromatography (ethyl acetate/n-hexane=½) to obtain 140.6 mg of the desired compound as a reddish brown solid (yield 59.0%).

$^1$H NMR (300 MHz, CDCl$_3$): δ 3.77 (s, 2H), 6.66 (d, J=5.54 Hz, 1H), 6.78 (d, J=8.82 Hz, 2H), 6.98 (d, J=8.79 Hz, 2H), 7.63 (t, J=7.16 Hz, 1H), 8.07 (dd, J=1.37, 7.49 Hz, 1H), 8.61 (dd, J=1.37, 9.81 Hz, 1H), 8.79 (d, J=5.25 Hz, 1H).

$^{13}$C NMR (75 MHz, CDCl$_3$): δ 104.80, 116.27, 122.06, 122.59, 124.31, 124.43, 126.38, 140.95, 144.74, 145.31, 148.15, 153.60, 162.79.

Step (3): Preparation of 1-[4-(8-nitroquinolin-4-yloxy)phenyl]-3-(4-chloro-3-trifluoromethylphenyl)urea (Compound of Formula 5)

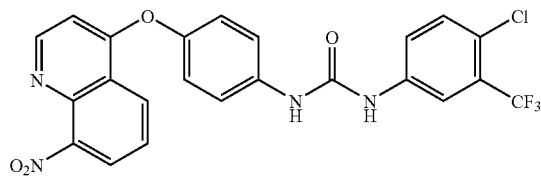

4-(8-Nitroquinolin-4-yloxy)phenylamine (7.5 mg, 0.027 mmol) and 4-chloro-3-(trifluoromethyl)phenyl isocyanate (11.8 mg, 0.054 mmol) were dissolved in tetrahydrofuran, and stirred at room temperature for 12 hours. When the reaction was completed, the solvent was removed by vacuum distillation, and a white solid product was filtered to obtain 12.0 mg of the desired compound (yield 88.9%).

$^1$H NMR (400 MHz, DMSO-d$_6$): δ 6.77 (d, J=5.24 Hz, 1H), 7.27 (d, J=17.11 Hz, 2H), 7.64-7.69 (m, 4H), 7.81 (t, J=8.06 Hz, 1H), 8.14 (s, 1H), 8.33 (d, J=8.00 Hz, 1H), 8.60 (d, J=8.00 Hz, 1H), 8.80 (d, J=5.22 Hz, 1H), 9.23 (s, 1H), 9.42 (s, 1H).

$^{13}$C NMR (100 MHz, DMSO-d$_6$): δ 105.92, 117.24, 120.90, 122.05, 122.78, 123.59, 124.24, 125.95, 126.10, 127.01, 127.31, 132.48, 137.92, 139.85, 140.31, 148.25, 148.48, 152.99, 154.31, 162.03.

Step (4): Preparation of 1-[4-(8-aminoquinolin-4-yloxy)phenyl]-3-(4-chloro-3-trifluoromethylphenyl)urea (Compound of Formula 6)

1-[4-(8-Nitroquinolin-4-yloxy)phenyl]-3-(4-chloro-3-trifluoromethylphenyl)urea (12.0 mg, 0.027 mmol) and tin (II) chloride (25.9 mg, 0.11 mmol) were dissolved in ethanol (0.23 mL), and then refluxed with stirring for 30 minutes. When the reaction was completed, the solvent was removed by vacuum distillation, the resultant was extracted with ethyl acetate and saturated sodium bicarbonate. Combined organic layers were dried with anhydrous sodium sulfate, and then filtered. The solvent was removed and then filtered a brown solid product to obtain 8.1 mg of the desired compound (yield 75.0%).

$^1$H NMR (400 MHz, DMSO-d$_6$): δ 5.93 (s, 1H), 6.53 (d, J=5.06 Hz, 1H), 6.89 (dd, J=1.38, 7.45 Hz, 1H), 7.18 (dd, J=2.06, 6.87 Hz, 2H), 7.30 (t, J=7.57 Hz, 1H), 7.37 (dd, J=1.32, 8.25 Hz, 1H), 7.58-7.67 (m, 4H), 8.12 (d, J=2.42 Hz, 1H), 8.50 (d, J=5.07 Hz, 1H), 9.17 (s, 1H), 9.39 (s, 1H).

$^{13}$C NMR (100 MHz, DMSO-d$_6$): δ 104.23, 106.82, 109.32, 116.66, 116.72, 120.32, 121.13, 121.27, 122.19, 123.00, 126.75, 127.13, 131.91, 136.65, 138.73, 139.29, 145.15, 147.55, 148.61, 152.40, 161.21.

Example 2

Preparation of N-[4-(8-aminoquinolin-4-yloxy]phenyl]-4-chloro-3-trifluoromethylbenzamide (Compound 1b)

Step (3): Preparation of N-[4-(8-nitroquinolin-4-yloxy]phenyl]-4-chloro-3-trifluoromethylbenzamide (Compound of Formula 5)

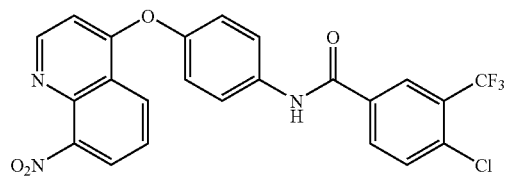

4-(8-Nitroquinolin-4-yloxy)phenylamine (103 mL, 0.46 mmol), N-hydroxybenzotriazole (HOBt) (62 mg, 0.46 mmol), 1-(3-dimethylaminopropyl)-3-ethylcarboimide (EDCl) (102 mg, 0.53 mmol) and 4-chloro-3-trifluoromethylbenzoic acid (103 mg, 0.46 mmol) were dissolved in dimethylformamide (3.6 mL), and to which triethylamine was added dropwise at room temperature, which was then heated and stirred at 80° C. When the reaction was completed, the resultant was extracted with ethyl acetate and saturated sodium bicarbonate, combined organic layers were dried with anhydrous sodium sulfate, and then filtered. The solvent was removed by vacuum distillation, and the residue was purified by a column chromatography (ethyl acetate/n-hexane=½) to obtain 125 mg of the desired compound as a brown solid (yield 71.2%).

$^1$H NMR (400 MHz, DMSO-d$_6$): δ 6.81 (d, J=5.2 Hz, 1H), 7.39 (s, 1H), 7.41 (s, 1H), 7.82 (t, J=1.50 Hz, 1H), 7.62-7.97 (m, 3H), 8.27 (dd, J=2.03, 13.17 Hz, 1H), 8.32 (dd, J=1.21, 10.86 Hz, 1H), 8.42 (d, J=1.96 Hz, 1H), 8.61 (dd, J=1.33, 8.47 Hz, 1H), 8.82 (d, J=5.24 Hz, 1H), 10.72 (s, 1H).

$^{13}$C NMR (100 MHz, DMSO-d$_6$): δ 105.61, 121.41, 121.52, 122.36, 123.78, 123.97, 125.64, 126.20, 127.04, 127.09, 131.94, 133.38, 133.96, 134.64, 136.73, 139.85, 147.98, 149.17, 153.80, 161.30, 163.19.

Step (4): Preparation of N-[4-(8-aminoquinolin-4-yloxy)phenyl]-4-chloro-3-trifluoromethylbenzamide (Compound of Formula 6: Compound 1b)

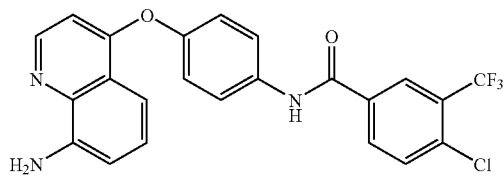

Synthetic procedure was performed in the same manner as done in step (4) (Formula 6/Compound 1a) of Example 1 to obtain the desired compound as a brown solid.

Yield: 26.0%

$^1$H NMR (300 MHz, DMSO-$d_6$): δ 6.00 (s, 2H), 6.60 (d, J=5.01 Hz, 1H), 6.95 (d, J=7.27 Hz, 1H), 7.29-7.42 (m, 4H), 7.92-7.96 (m, 3H), 8.31 (d, J=8.33 Hz, 1H), 8.44 (s, 1H), 8.55 (d, J=5.02 Hz, 1H).

$^{13}$C NMR (75 MHz, DMSO-$d_6$): δ 121.31, 121.56, 121.77, 121.77, 122.80, 122.90, 124.93, 126.95, 127.37, 127.57, 127.64, 127.75, 132.40, 133.83, 134.42, 134.44, 134.50, 136.54, 139.36, 146.05, 148.09.

Example 3

Preparation of 1-[4-(8-acetylaminoquinolin-4-yloxy)phenyl]-3-(4-chloro-3-trifluoromethyphenyl)urea (Step (5): Compound 1c)

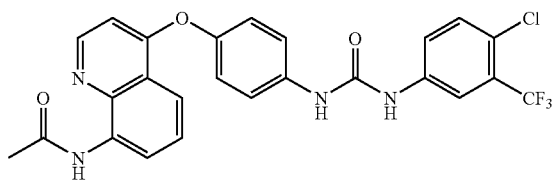

Synthetic procedure was performed in the same manner as done in step (3) (preparation of compound of Formula 5) of Example 2 to obtain the desired compound as a white solid.

Yield: 81.0%

$^1$H NMR (400 MHz, DMSO-$d_6$): δ 2.28 (s, 3H), 6.69 (d, J=5.15 Hz, 1H), 7.27 (d, J=8.94 Hz, 1H), 7.59-7.71 (m, 5H), 7.98 (dd, J=1.16, 8.36 Hz, 1H), 8.13 (d, J=2.21 Hz, 1H), 8.64 (d, J=7.57 Hz, 1H), 8.71 (d, J=5.18 Hz, 1H), 9.11 (s, 1H), 9.30 (s, 1H), 10.12 (s, 1H).

$^{13}$C NMR (100 MHz, DMSO-$d_6$): δ 25.00, 105.10, 115.55, 117.24, 117.74, 120.91, 121.67, 121.84, 122.81, 123.58, 127.08, 127.31, 130.15, 132.48, 135.16, 137.53, 129.78, 140.02, 148.71, 150.20, 152.94, 162.20, 169.47.

Example 4

Preparation of N-[3-(8-acetylaminoquinolin-4-yloxy)-4-methylphenyl]-4-chloro-3-trifluoromethyl-benzamide (Compound 1k)

Step (1): Preparation of [3-(8-nitroquinolin-4-yloxy)-4-methylphenyl]-t-butylcarbamate (Compound of Formula 7)

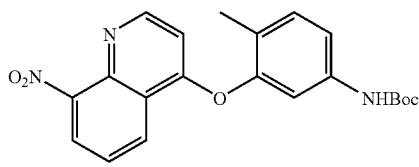

Synthetic procedure was performed in the same manner as done in step (2) (Formula 4) of Example 1 to obtain the desired compound as a white solid.

Yield: 67.7%

$^1$H-NMR (400 MHz, CDCl$_3$): δ 1.48 (s, 9H), 2.08 (s, 3H), 6.54 (d, J=5.17 Hz, 1H), 6.78 (s, 1H), 7.10 (d, J=8.24 Hz, 1H), 7.24 (d, J=8.28 Hz, 1H), 7.44 (s, 1H), 7.65 (t, J=7.65 Hz, 1H), 8.08 (d, J=7.46 Hz, 1H), 8.62 (d, J=8.43 Hz, 1H), 8.77 (d, J=5.15 Hz, 1H).

$^{13}$C NMR (100 MHz, CDCl$_3$): δ 15.21, 28.27, 80.87, 104.57, 111.76, 116.44, 122.22, 124.39, 124.46, 124.63, 126.26, 132.10, 138.30, 140.92, 148.09, 151.60, 152.62, 153.62, 161.25.

Step (2): Preparation of [3-(8-aminoquinolin-4-yloxy)-4-methylphenyl]-t-butylcarbamate (Compound of Formula 8)

3-(8-Nitroquinolin-4-yloxy)-4-methylphenyl]-t-butylcarbamate (26.3 mg, 0.06 mmol) was dissolved in methanol, to which 5% palladium charcoal (28.5 mg, 0.013 mmol) was added thereto, which was then stirred at room temperature for three hours. When the reaction was completed, the resultant was filtered using celite to remove the palladium charcoal. The solvent was removed by vacuum distillation, and the residue was purified by a column chromatography (ethyl acetate/n-hexane=½) to obtain 16.0 mg of the desired compound as a brown solid (yield 73.0%).

$^1$H NMR (400 MHz, CDCl$_3$): δ 1.49 (s, 9H), 2.10 (s, 3H), 4.98 (s, 2H), 6.39 (d, J=5.06 Hz, 1H), 6.49 (s, 1H), 6.84 (d, J=7.47 Hz, 1H), 7.14 (d, J=8.30 Hz, 1H), 7.22 (d, J=8.22 Hz, 1H), 7.36 (t, J=7.65 Hz, 1H), 7.68 (d, J=8.21 Hz, 1H), 8.49 (d, J=5.07 Hz, 1H).

13C NMR (100 MHz, CDCl3): δ 15.31, 28.33, 80.79, 103.68, 110.03, 110.87, 112.06, 115.88, 121.57, 125.02, 126.77, 131.90, 137.88, 139.81, 143.75, 148.15, 152.50, 152.58, 161.34.

Step (3): Preparation of [3-(8-acetylaminoquinolin-4-yloxy)-4-methylphenyl]-t-butylcarbamate (Compound of Formula 9)

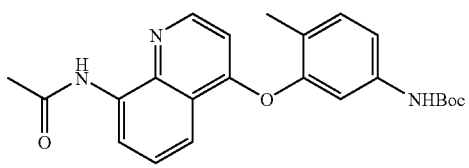

Synthetic procedure was performed in the same manner as done in step (3) (Formula 5) of Example 2 to obtain the desired compound as a white solid.

Yield: 82.0%

1H NMR (400 MHz, DMSO-d6): δ 1.43 (s, 9H), 2.02 (s, 3H), 2.26 (s, 3H), 6.54 (d, J=5.12 Hz, 1H), 7.32-7.33 (m, 2H), 7.37 (s, 1H), 7.61 (t, J=8.04 Hz, 1H), 7.90 (dd, J=1.24, 8.40 Hz, 1H), 8.66-8.69 (m, 2H), 9.51 (s, 1H), 10.10 (s, 1H).

13C NMR (100 MHz, DMSO-d6): δ 14.74, 24.52, 28.03, 79.28, 104.13, 104.13, 110.66, 114.95, 115.78, 117.30, 120.15, 122.82, 126.69, 131.83, 134.75, 139.23, 139.55, 149.81, 151.46, 152.63, 160.67, 168.95.

Step (4): Preparation of [3-(8-acetylaminoquinolin-4-yloxy)-4-methylphenyl]amine (Compound of Formula 10)

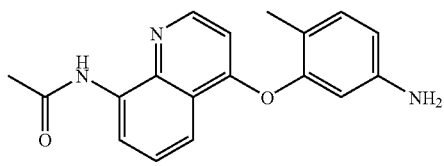

3-(8-Acetylaminoquinolin-4-yloxy)-4-methylphenyl-t-butylcarbamate (120 mg, 0.26 mmol) was dissolved in a 1:1 (by volume) mixture of dichloromethane and trifluoroacetic acid, which was then stirred at room temperature for one hour. When the reaction was completed, the resultant was neutralized with 1 M sodium hydroxide. The resultant was extracted with dichloromethane and water, and combined organic layers were dried with anhydrous sodium sulfate, and then filtered. After the solvent was removed by vacuum distillation, filtered a brown solid product to obtain 86 mg of the desired compound (yield 88.6%).

1H NMR (400 MHz, DMSO-d6): δ 1.90 (s, 3H), 2.18 (s, 3H), 5.19 (s, 2H), 6.37 (s, 1H), 6.50 (d, J=9.42 Hz, 1H), 6.57 (d, J=5.08 Hz, 1H), 7.04 (d, J=8.20 Hz, 1H), 7.60 (t, J=7.92 Hz, 1H), 7.98 (d, J=8.48 Hz, 1H), 8.66-8.70 (m, 2H), 10.11 (s, 1H).

13C NMR (100 MHz, DMSO-d6): δ 14.97, 25.02, 104.65, 106.69, 112.55, 115.51, 115.90, 117.68, 120.75, 127.01, 132.46, 135.21, 140.02, 149.30, 150.30, 152.58, 161.43, 169.41.

Step (5): Preparation of N-[3-(8-acetylaminoquinolin-4-yloxy)-4-methylphenyl]-4-chloro-3-trifluoromethylbenzamide (Compound 1k)

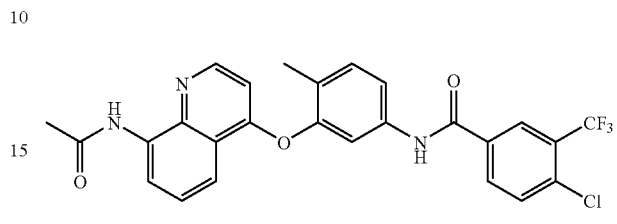

Synthetic procedure was performed in the same manner as done in step (3) (Formula 5) of Example 2 to obtain the desired compound as a yellow solid.

Yield: 91.0%

1H NMR (400 MHz, DMSO-d6): δ 2.10 (s, 3H), 2.28 (s, 3H), 6.62 (d, J=5.05 Hz, 1H), 7.41 (d, J=8.31 Hz, 1H), 7.60 (t, J=8.01 Hz, 1H), 7.67 (d, J=8.17 Hz, 1H), 7.72 (s, 1H), 7.88 (d, J=8.38 Hz, 1H), 8.01 (d, J=8.24 Hz, 1H), 8.22 (d, J=8.26 Hz, 1H), 8.35 (s, 1H), 8.68-8.70 (m, 2H), 10.10 (s, 1H), 10.61 (s, 1H).

13C NMR (100 MHz, DMSO-d6): δ 15.42, 24.99, 104.87, 113.53, 115.40, 117.76, 118.42, 120.74, 125.69, 127.20, 127.27, 127.42, 127.27, 132.15, 132.35, 133.75, 134.27, 134.48, 135.26, 138.83, 140.08, 150.19, 151.97, 161.12, 163.51, 169.37.

MS m/z 514.50 (M+H)+.

Examples 5 to 19

The compounds of Examples 5 to 19 below were obtained in the same manner as those described in Examples 1 to 4. The results of the structure identification are presented below.

Example 5

N-[4-(8-acetylaminoquinolin-4-yloxy)phenyl]-4-chloro-3-trifluoromethylbenzamide (Compound 1d)

Yield: 42.3%

1H NMR (400 MHz, DMSO-d6): δ 6.73 (d, J=5.18 Hz, 1H), 7.36 (dd, J=2.31, 6.90 Hz, 2H), 7.62 (t, J=16.12 Hz, 1H), 7.90-8.00 (m, 4H), 8.30 (dd, J=1.89, 8.42 Hz, 1H), 8.42 (d, J=1.86 Hz, 1H), 8.69 (d, J=7.67 Hz, 1H), 8.73 (d, J=5.16 Hz, 1H), 10.13 (s, 1H), 10.71 (s, 1H).

13C NMR (100 MHz, DMSO-d6): δ 25.02, 105.39, 115.53, 120.99, 121.85, 122.85, 124.53, 124.64, 126.78, 127.17, 127.99, 128.04, 130.25, 132.47, 133.89, 134.27, 134.52, 135.21, 136.90, 139.72, 142.39, 153.16, 161.97, 163.68, 169.45.

Example 6

N-[4-(8-benzoylaminoquinolin-4-yloxy)phenyl]-4-chloro-3-trifluoromethylbenzamide (Compound 1e)

Yield: 61.4%

1H NMR (300 MHz, DMSO-d6): δ 6.76 (d, J=5.17 Hz, 1H), 7.37 (d, J=8.94 Hz, 1H), 7.62-7.73 (m, 4H), 7.94-7.96 (m,

3H), 8.04-8.07 (m, 3H), 8.28-8.31 (m 1H), 8.42 (s, 1H), 8.77 (d, J=5.20 Hz, 1H), 8.82 (d, J=7.55 Hz, 1H), 10.70 (s, 1H).
$^{13}$C NMR (100 MHz, DMSO-$d_6$): δ 105.58, 116.19, 117.56, 120.97, 121.85, 122.84, 127.00, 127.23, 127.48, 129.53, 132.43, 132.65, 133.86, 134.47, 134.87, 136.99, 140.28, 150.05, 150.64, 162.16, 163.63, 164.95.
MS m/z 562.50 (M+H)$^+$.

Example 7

1-[3-(8-aminoquinolin-4-yloxy)phenyl]-3-(4-chloro-3-trifluoromethylphenyl)urea (Compound 1f)

Yield: 85.0%
$^1$H NMR (400 MHz, DMSO-$d_6$): δ 5.97 (s, 2H), 6.67 (d, J=5.06 Hz, 1H), 6.88 (dd, J=2.07, 8.02 Hz, 1H), 6.92 (dd, J=2.01, 6.74 Hz, 1H), 7.30-7.36 (m, 3H) 7.42 (t, J=16.22 Hz, 1H), 7.48 (s, 1H), 7.59-7.69 (m, 2H), 8.07 (d, J=1.91 Hz, 1H), 8.55 (d, J=5.01 Hz, 1H), 9.12 (s, 1H), 9.25 (s, 1H).
$^{13}$C NMR (100 MHz, DMSO-$d_6$): δ 105.83, 107.34, 109.89, 110.78, 114.51, 115.75, 117.37, 121.91, 122.96, 123.66, 127.86, 131.02, 132.45, 139.40, 139.61, 141.69, 145.75, 148.12, 152.78, 155.24, 161.05.

Example 8

N-[3-(8-aminoquinolin-4-yloxy)phenyl]-4-chloro-3-trifluoromethylbenzamide (Compound 1g)

Yield: 65.1%
$^1$H NMR (400 MHz, DMSO-$d_6$): δ 6.69 (d, J=8.80 Hz, 1H), 6.91-6.93 (m, 1H), 7.04 (d, J=8.62 Hz, 1H), 7.01-7.36 (m, 2H), 7.51 (t, J=16.7 Hz, 1H), 7.67-7.69 (m, 2H), 7.92 (d, J=8.48 Hz, 1H), 8.24 (d, J=8.37 Hz, 1H), 8.37 (s, 1H), 8.57 (d, J=4.96 Hz, 1H), 10.66-10.70 (m, 1H).
$^{13}$C NMR (100 MHz, DMSO-$d_6$): δ 106.23, 107.29, 109.93, 112.19, 116.39, 117.44, 122.00, 127.54, 127.59, 127.97, 131.02, 132.44, 133.90, 134.36, 134.53, 139.44, 141.01, 145.84, 148.14, 155.21, 160.91, 163.81, 170.81.

Example 9

1-[3-(8-acetylaminoquinolin-4-yloxy)phenyl]-3-(4-chloro-3-trifluoromethylphenyl)urea (Compound 1h)

Yield: 31.0%
$^1$H NMR (400 MHz, DMSO-$d_6$): δ 2.24 (s, 3H), 6.77 (d, J=9.16 Hz, 1H), 6.95 (dd, J=1.80, 7.80 Hz, 1H), 7.35 (d, J=7.88 Hz, 1H), 7.44 (t, J=20.36 Hz, 1H), 7.57-7.64 (m, 4H), 7.97 (d, J=8.36 Hz, 1H), 8.09 (d, J=1.8 Hz, 1H), 8.69 (d, J=7.64 Hz, 1H), 8.74 (d, J=5.12 Hz, 1H), 9.14 (s, 1H), 9.27 (s, 1H), 10.13 (s, 1H).
$^{13}$C NMR (100 MHz, DMSO-$d_6$): δ 24.52, 105.38, 110.58, 114.27, 114.20, 115.72, 116.89, 117.25, 120.59, 122.50, 123.18, 126.52, 126.72, 130.63, 131.95, 134.74, 139.09, 139.63, 141.30, 149.69, 152.29, 154.21, 161.08, 168.92.
MS m/z 515.47 (M+H)$^+$.

Example 10

N-[3-(8-acetylaminoquinolin-4-yloxy)phenyl]-4-chloro-3-trifluoromethylbenzamide (Compound 1i)

Yield: 30.4%
$^1$H NMR (300 MHz, DMSO-$d_6$): δ 2.28 (s, 3H), 6.82 (d, J=5.12 Hz, 1H), 7.09-7.12 (m, 1H), 7.52-7.77 (m. 4H), 7.95 (t, J=17.63 Hz, 1H), 8.24 (d, J=8.57 Hz, 1H), 8.37 (s, 1H), 8.68 (d, J=7.52 Hz, 1H), 8.76 (d, J=5.12 Hz, 1H), 10.14 (s, 1H), 10.71 (s, 1H).
$^{13}$C NMR (100 MHz, DMSO-$d_6$): δ 25.02, 1056.17, 112.86, 115.48, 116.72, 117.83, 117.93, 119.02, 121.14, 126.98, 127.32, 127.58, 131.16, 132.46, 133.90, 134.31, 134.57, 135.28, 140.16, 141.11, 150.22, 154.61, 161.46, 163.84, 169.45.

Example 11

N-[3-(8-benzoylaminoquinolin-4-yloxy)phenyl]-4-chloro-3-trifluoromethylbenzamide (Compound 1j)

Yield: 30.0%
$^1$H NMR (400 MHz, DMSO-$d_6$): δ 6.85 (d, J=5.13 Hz, 1H), 7.12 (d, J=8.05 Hz, 1H), 7.52-7.73 (m, 7H), 7.79 (s, 1H), 7.92 (d, J=8.36 Hz, 1H), 8.02-8.10 (m, 2H), 8.53 (d, J=8.52 Hz, 1H), 8.36 (s, 1H), 8.79-8.82 (m, 2H), 10.69 (s, 2H).
$^{13}$C NMR (100 MHz, DMSO-$d_6$): δ 105.90, 112.39, 115.66, 116.24, 117.21, 117.52, 120.64, 126.79, 126.95, 127.01, 127.86, 128.54, 129.06, 130.71, 131.97, 132.20, 133.41, 133.82, 134.09, 134.35, 139.90, 140.63, 150.23, 154.04, 154.34, 161.18, 163.36, 164.52.

Example 12

N-[3-(8-acetylaminoquinolin-4-yloxy)-4-methylphenyl]-3-trifluoromethylbenzamide (Compound 1l)

Yield: 74.6%
$^1$H NMR (400 MHz, DMSO-$d_6$): δ 2.12 (s, 3H), 2.28 (s, 3H), 6.64 (d, J=5.12 Hz, 1H), 7.44 (d, J=10.06 Hz, 1H), 7.61-7.80 (m, 5H), 7.96 (d, J=7.72 Hz, 1H), 8.03 (dd, J=1.02, 8.42 Hz, 1H), 8.23 (d, J=7.89 Hz, 1H), 8.27 (s, 1H), 8.68 (d, J=7.62 Hz, 1H), 8.72 (d, J=5.14 Hz, 1H), 10.12 (s, 1H), 10.59 (s, 1H).
$^{13}$C NMR (75 MHz, DMSO-$d_6$): δ 15.45, 25.00, 104.98, 113.52, 115.45, 117.84, 118.45, 120.78, 122.60, 124.63, 125.60, 126.21, 127.26, 128.67, 130.23, 132.28, 132.35, 135.27, 135.99, 138.95, 140.12, 150.28, 152.01, 161.12, 164.52, 169.42.

Example 13

N-[3-(8-acetylaminoquinolin-4-yloxy)-4-methylphenyl]-3,5-bistrifluoromethylbenzamide (Compound 1m)

Yield: 26.0%
$^1$H NMR (300 MHz, DMSO-$d_6$): δ 2.14 (s, 1H), 2.28 (s, 1H), 6.65 (d, J=5.08 Hz, 1H), 7.47 (d, J=8.81 Hz, 1H), 7.61-7.70 (m, 3H), 8.02 (d, J=8.78 Hz, 1H), 8.37 (s, 1H), 8.58 (s, 2H), 8.68 (d, J=7.76 Hz, 1H), 8.72 (d, J=5.09 Hz, 1H), 10.12 (s, 1H), 10.76 (s, 1H).
$^{13}$C NMR (75 MHz, DMSO-$d_6$): δ 15.47, 25.00, 105.04, 113.67, 115.45, 117.87, 118.58, 120.79, 121.74, 125.36, 126.01, 127.30, 128.98, 130.30, 130.74, 131.19, 131.63, 132.44, 135.27, 137.33, 138.59, 140.14, 150.28, 152.09, 161.10, 163.02, 169.44.
MS m/z 548.53 (M+H)$^+$.

Example 14

N-[3-(8-acetylaminoquinolin-4-yloxy)-4-methylphenyl]-4-nitro-3-trifluoromethylbenzamide (Compound 1n)

Yield: 44.2%
$^1$H NMR (400 MHz, DMSO-d$_6$): δ 2.12 (s, 3H), 2.26 (s, 3H), 6.62 (d, J=5.12 Hz, 1H), 7.44 (d, J=8.34 Hz, 1H), 7.59-7.69 (m, 4H), 8.00 (d, J=8.33 Hz, 1H), 8.30 (d, J=8.20 Hz, 1H), 8.42 (d, J=8.45 Hz, 1H), 8.47 (s, 1H), 8.67 (d, J=7.66 Hz, 1H), 8.70 (d, J=5.14 Hz, 1H), 10.10 (s, 1H), 10.76 (s, 1H).
$^{13}$C NMR (75 MHz, DMSO-d$_6$): δ 15.43, 24.94, 104.98, 113.57, 115.52, 117.93, 118.53, 120.76, 121.64, 122.08, 124.12, 126.13, 126.18, 127.28, 127.68, 132.46, 134.25, 135.16, 138.483, 139.12, 140.111, 149.12, 150.30, 152.04.

Example 15

N-[3-(8-acetylaminoquinolin-4-yloxy)-4-methylphenyl]-3-(4-hydroxypiperidin-1-yl)-5-trifluoromethylbenzamide (Compound 1o)

Yield: 41.0%
$^1$H NMR (400 MHz, DMSO-d$_6$): δ 1.42-4.49 (m, 2H), 1.81-1.84 (m, 1H), 2.11 (s, 3H), 2.27 (s, 3H), 2.98 (m, 2H), 3.66-3.69 (m, 4H), 4.71 (d, J=3.92 Hz, 1H), 6.62 (d, J=5.06 Hz, 1H), 7.33 (s, 1H), 7.42 (d, J=8.18 Hz, 1H), 7.53 (s, 1H), 7.60-7.69 (m, 4H), 8.02 (d, J=8.35 Hz, 1H), 8.67-8.71 (m, 2H), 10.11 (s, 1H), 10.42 (s, 1H).
$^{13}$C NMR (100 MHz, DMSO-d$_6$): δ 14.95, 24.51, 33.39, 45.62, 65.62, 104.43, 112.79, 113.16, 113.58, 114.97, 117.36, 117.44, 118.08, 120.26, 122.75, 125.02, 126.76, 131.80, 134.76, 136.39, 138.51, 139.23, 139.61, 149.80, 151.08, 151.46, 160.65, 164.59, 168.96.

Example 16

N-[3-(8-acetylaminoquinolin-4-yloxy)-4-methylphenyl]-3-(4-methylimidazol-1-yl)-5-trifluoromethylbenzamide (Compound 1p)

Yield: 41.0%
$^1$H NMR (400 MHz, DMSO-d$_6$): δ 2.10 (s, 1H), 2.15 (s, 1H), 2.26 (s, 1H), 6.62 (d, J=5.12 Hz, 1H), 7.43 (d, J=8.28 Hz, 1H), 7.60 (t, J=8.15 Hz, 1H), 7.66-7.68 (m, 3H), 7.99 (d, J=8.24 Hz, 1H), 8.12 (s, 1H), 8.21 (s, 1H), 8.36 (s, 1H), 8.39 (s, 1H), 8.66 (d, J=7.70 Hz, 1H), 8.70 (d, J=5.12 Hz, 1H), 10.09 (s, 1H), 10.58 (s, 1H).
$^{13}$C NMR (100 MHz, DMSO-d$_6$): δ 14.00, 15.47, 25.00, 104.99, 113.55, 114.69, 115.45, 117.85, 118.47, 119.67, 120.78, 122.30, 123.04, 125.84, 127.28, 131.15, 131.48, 132.42, 135.27, 135.70, 137.78, 138.20, 138.74, 139.44, 140.13, 150.26, 152.07, 161.11, 163.71, 169.44.

Example 17

N-[3-(8-acetylaminoquinolin-4-yloxy)-4-methylphenyl]-2-chlorobenzamide (Compound 1q)

Yield: 28.9%
$^1$H NMR (400 MHz, DMSO-d$_6$): δ 2.10 (s, 3H), 2.27 (s, 3H), 6.62 (d, J=8.32 Hz, 1H), 7.53 (d, J=8.08 Hz, 1H), 7.60-7.66 (m, 3H), 8.00 (d, J=8.36 Hz, 1H), 8.65-8.78 (m, 4H), 10.11 (s, 1H), 10.85 (m, 1H).
$^{13}$C NMR (75 MHz, DMSO-d$_6$): δ 14.98, 24.50, 104.47, 112.27, 114.96, 117.29, 120.23, 122.74, 125.50, 126.79, 127.31, 132.13, 134.77, 137.96, 139.62, 142.96, 148.47, 149.48, 149.80, 151.62, 160.50, 162.81, 168.93.

Example 18

N-[3-(8-acetylaminoquinolin-4-yloxy)-4-methylphenyl]-5-methylisoxazole-3-carboxylic acid amide (Compound 1r)

Yield: 73.7%
$^1$H NMR (400 MHz, DMSO-d$_6$): δ 2.10 (s, 3H), 2.27 (s, 3H), 2.48 (s, 3H), 6.61-6.63 (m, 2H), 7.41 (d, J=7.72 Hz, 1H), 7.60-7.72 (m, 3H), 8.00 (d, J=7.50 Hz, 1H), 8.67-8.71 (m, 2H), 10.11 (s, 1H), 10.78 (s, 1H).
$^{13}$C NMR (100 MHz, DMSO-d$_6$): δ 12.28, 15.42, 24.95, 102.01, 104.91, 113.54, 115.55, 117.93, 118.52, 120.72, 126.05, 127.26, 132.43, 135.15, 138.09, 140.09, 150.34, 151.90, 158.01, 159.50, 161.03, 169.61, 172.07.

Example 19

N-[3-(8-benzoylaminoquinolin-4-yloxy)-4-methylphenyl]-4-chloro-3-trifluoromethylbenzamide (Compound 1s)

Yield: 44.0%
$^1$H NMR (400 MHz, DMSO-d$_6$): δ 2.13 (s, 3H), 6.67 (d, J=5.16 Hz, 1H), 7.44 (d, J=8.36 Hz, 1H), 7.60-7.74 (m, 7H), 7.91 (d, J=8.44 Hz, 1H), 8.02-8.04 (m, 2H), 8.10 (d, J=8.44 Hz, 1H), 8.23 (d, J=8.36 Hz, 1H), 8.36 (s, 1H), 8.76 (d, J=5.16 Hz, 1H), 8.80 (d, J=7.64 Hz, 1H), 10.64 (s, 1H), 10.69 (s, 1H).
$^{13}$C NMR (100 MHz, DMSO-d$_6$): δ 15.47, 100.84, 105.17, 113.56, 116.12, 117.72, 118.54, 120.75, 121.72, 124.44, 125.76, 126.97, 127.39, 127.50, 129.20, 129.55, 132.44, 132.68, 133.83, 134.33, 134.49, 134.59, 134.85, 138.82, 140.34, 150.76, 151.93, 161.31, 163.63, 165.01.

Example 20

Experimentation of Anti-Proliferative Effect on Melanoma Tumor Cells

10% of fetal bovine serum (FBS) and 1% of penicillin/streptomycin were put into a Dulbecco's Modified Eagle (DMEM) medium, and A375P tumor cells obtained from ATCC was incubated in the above medium under a 5% CO$_2$ atmosphere at 37° C. A375P cells were taken into 0.05% trypsin-0.02% ethylene-diamine tetraacetic acid (EDTA) and seeded it into wells of 96 well plate with 5×10$^3$ cells/well, and the viability of the cells was determined with a conventional [3-(4,5-dimethylthiazol-2-yl)-2,5-diphenyltetrazolium bromide, MTT] reduction assay. In the MTT efficacy experimentation, 15 μL of dye per well was put into the wells in accordance with the protocol of CellTiter 96® Assay (Promega), and then incubated for two hours, into which 100 μL of stop solution was added. The resultant was read after 24 hours. After one day of the plating, the obtained material was treated with a compound of the present invention. When it was treated with the compound, 10 mM of stock solution was prepared, and gradually diluted to one-third in dimethyl sulfoxide (DMSO). A test compound plate was prepared with 12 points, into which 0.5 μL was put (final concentration was DMSO 0.5%). Absorbance was read at a wavelength of 590 nm using EnVision 2103 (Perkin Elmer Boston, Mass., US), and GI$_{50}$ values were calculated using GraphPad Prism 4.0 software.

GI$_{50}$ values indicating inhibition of the compounds according to the examples of the present invention and control substances, on the proliferation of A375 melanoma tumor cells and HS27 fibroblasts. Sorafenib (BAY43-9006, Nexavar) which has been known as a substance having a good anti-proliferative effect on the melanoma tumor cells was used as a control substance.

TABLE 1a
| Compound | Orientation | R¹ | R² | R³ | GI$_{50}$ (μM) A375 | HS27 |
|---|---|---|---|---|---|---|
| 1a | p-Phenyl | NH$_2$ | 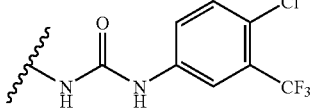 | H | 3.74 | 6.71 |
| 1b | p-Phenyl | NH$_2$ | 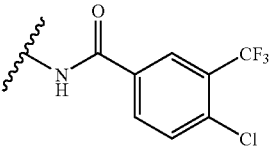 | H | 5.69 | 7.63 |
| 1c | p-Phenyl | CH$_3$CONH | 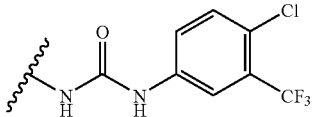 | H | 4.19 | 6.02 |
| 1d | p-Phenyl | CH$_3$CONH | 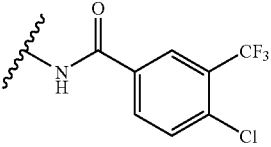 | H | 3.14 | 5.47 |
| 1e | p-Phenyl | C$_6$H$_5$CONH | 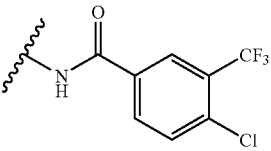 | H | 0.80 | >20 |
| 1f | m-Phenyl | NH$_2$ | 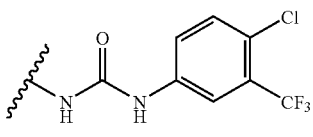 | H | 2.56 | 10.39 |
| 1g | m-Phenyl | NH$_2$ | 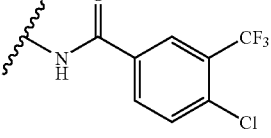 | H | 6.73 | >20 |
| 1h | m-Phenyl | CH$_3$CONH | 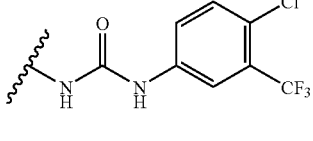 | H | 2.32 | 5.68 |
| 1i | m-Phenyl | CH$_3$CONH | 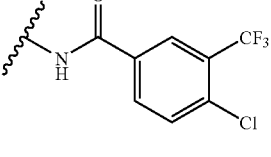 | H | 3.49 | >20 |
| 1j | m-Phenyl | C$_6$H$_5$CONH | 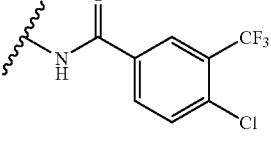 | H | 0.78 | >20 |

TABLE 1a-continued
| Compound | Orientation | R[1] | R[2] | R[3] | GI$_{50}$ (µM) A375 | HS27 |
|---|---|---|---|---|---|---|
| 1k | m-Phenyl | CH$_3$CONH | 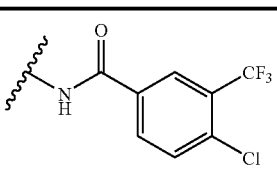 | CH$_3$ | 1.30 | >20 |
| 1l | m-Phenyl | CH$_3$CONH | 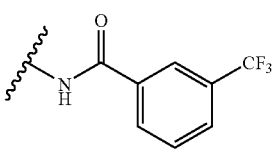 | CH$_3$ | 1.28 | >20 |
TABLE 1b
| Compound | Orientation | R[1] | R[2] | R[3] | GI$_{50}$ (µM) A375 | HS27 |
|---|---|---|---|---|---|---|
| 1m | m-Phenyl | CH$_3$CONH | 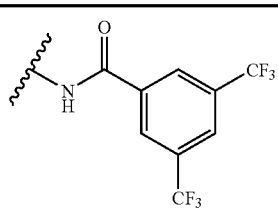 | CH$_3$ | 0.77 | >20 |
| 1n | m-Phenyl | CH$_3$CONH | 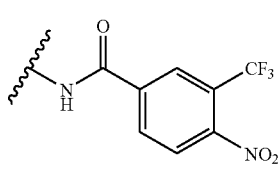 | CH$_3$ | 0.79 | >20 |
| 1o | m-Phenyl | CH$_3$CONH | 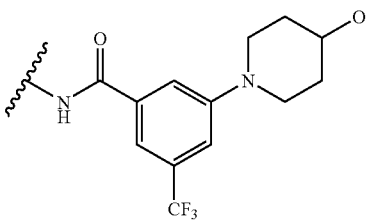 | CH$_3$ | >20 | >20 |
| 1p | m-Phenyl | CH$_3$CONH | 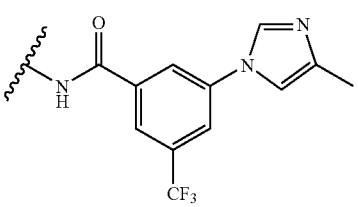 | CH$_3$ | >20 | >20 |
| 1q | m-Phenyl | CH$_3$CONH | 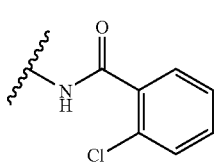 | CH$_3$ | 2.12 | >20 |

TABLE 1b-continued

| Compound | Orientation | R¹ | R² | R³ | GI₅₀ (μM) A375 | HS27 |
|---|---|---|---|---|---|---|
| 1r | m-Phenyl | $CH_3CONH$ | (N-H-C(=O)-5-methylisoxazol-3-yl) | $CH_3$ | >20 | >20 |
| 1s | m-Phenyl | $C_6H_5CONH$ | (N-H-C(=O)-3-CF₃-4-Cl-phenyl) 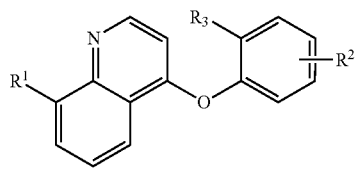 | $CH_3$ | 1.03 | >20 |
| Sorafenib | | | | | 5.58 | 7.85 |

As can be seen from Tables 1a and 1b above, among the nineteen compounds of the present invention, fourteen compounds have better anti-proliferative effect than sorafenib ($GI_{50}$=5.58), the control substance, on A375 melanoma tumor cells, and thirteen compounds exhibit excellent selectivity which do not inhibit proliferation of HS27 fibroblasts. In particular, $GI_{50}$ values of compounds 1e, 1j, 1m and 1n are in the range of 0.77 μM to 0.80 μM, which exhibit excellent anti-proliferative effect on A375 melanoma tumor cells.

As so far described, the aminoquinoline compound represented by Formula 1 or a pharmaceutically acceptable salt thereof have the excellent anti-proliferative effect on the melanoma tumor cells, it can be used as a therapeutic agent for preventing or treating cutaneous cancer.

What is claimed is:

1. An aminoquinoline compound represented by Formula 1 below, or a pharmaceutically acceptable salt thereof:

Formula 1:

[Structure of Formula 1: 8-substituted quinoline linked via 4-oxy to a phenyl ring bearing R² and R³]

wherein
R¹ is $NH_2$ or $NHCOR^4$;
R² is $NHCONHR^5$ or $NHCOR^5$;
R³ is H or $C_1$-$C_6$ alkyl;
R⁴ is $C_1$-$C_6$ alkyl or $C_6$-$C_{10}$ aryl;
R⁵ is $C_6$-$C_{10}$ aryl or $C_3$-$C_6$ heteroaryl which is unsubstituted or substituted with one or more substituents selected from the group consisting of $C_1$-$C_6$ alkyl; one or more halogen atoms selected from the group consisting of fluorine, chlorine, bromine and iodine; $C_1$-$C_6$ alkyl substituted with one or more halogen atoms selected from the group consisting of fluorine, chlorine, bromine and iodine; nitro; substituted or unsubstituted piperidinyl; substituted or unsubstituted imidazolyl; substituted or unsubstituted isoxazolyl; and substituted or unsubstituted morpholinyl, wherein the substituent on the piperidinyl, imidazolyl, isoxazolyl or morpholinyl is hydroxyl or $C_1$-$C_6$ alkyl.

2. The aminoquinoline compound or pharmaceutically acceptable salt thereof according to claim 1, wherein R⁴ is methyl or phenyl.

3. The aminoquinoline compound or pharmaceutically acceptable salt thereof according to claim 1, wherein R⁵ is unsubstituted phenyl; or phenyl substituted with at least one substituent selected from the group consisting of halogen; $C_1$-$C_6$ alkyl which is substituted with one or more halogen; nitro; hydroxyl piperidinyl; imidazolyl which is unsubstituted or substituted with $C_1$-$C_6$ alkyl; and isoxazolyl which is unsubstituted or substituted with $C_1$-$C_6$ alkyl.

4. The aminoquinoline compound or pharmaceutically acceptable salt thereof according to claim 1, selected from the group consisting of the compounds below:
1-[4-(8-aminoquinolin-4-yloxy)phenyl]-3-(4-chloro-3-trifluoromethylphenyl)urea;
N-[4-(8-aminoquinolin-4-yloxy)phenyl]-4-chloro-3-trifluoromethylbenzamide;
1-[4-(8-acetylaminoquinolin-4-yloxy)phenyl]-3-(4-chloro-3-trifluoromethyl-phenyl)urea;
N-[4-(8-acetylaminoquinolin-4-yloxy)phenyl]-4-chloro-3-trifluoromethylbenzamide;
N-[4-(8-benzoylaminoquinolin-4-yloxy)phenyl]-4-chloro-3-trifluoromethylbenzamide;
1-[3-(8-aminoquinolin-4-yloxy)phenyl]-3-(4-chloro-3-trifluoromethylphenyl)urea;
N-[3-(8-aminoquinolin-4-yloxy)phenyl]-4-chloro-3-trifluoromethylbenzamide;
1-[3-(8-acetylaminoquinolin-4-yloxy)phenyl]-3-(4-chloro-3-trifluoromethyl-phenyl)urea;
N-[3-(8-acetylaminoquinolin-4-yloxy)phenyl]-4-chloro-3-trifluoromethylbenzamide;
N-[3-(8-benzoylaminoquinolin-4-yloxy)phenyl]-4-chloro-3-trifluoromethylbenzamide;
N-[3-(8-acetylaminoquinolin-4-yloxy)-4-methylphenyl]-4-chloro-3-trifluoromethylbenzamide;
N-[3-(8-acetylaminoquinolin-4-yloxy)-4-methylphenyl]-3-trifluoromethylbenzamide;
N-[3-(8-acetylaminoquinolin-4-yloxy)-4-methylphenyl]-3,5-bistrifluoromethylbenzamide;
N-[3-(8-acetylaminoquinolin-4-yloxy)-4-methylphenyl]-4-nitro-3-trifluoromethylbenzamide;

N-[3-(8-acetylaminoquinolin-4-yloxy)-4-methylphenyl]-3-(4-hydroxypiperidin-1-yl)-5-trifluoromethylbenzamide;

N-[3-(8-acetylaminoquinolin-4-yloxy)-4-methylphenyl]-3-(4-methylimidazol-1-yl)-5-trifluoromethylbenzamide;

N-[3-(8-acetylaminoquinolin-4-yloxy)-4-methylphenyl]-2-chlorobenzamide;

N-[3-(8-acetylaminoquinolin-4-yloxy)-4-methylphenyl]-5-methylisoxazole-3-carboxylic acid amide; and N-[3-(8-benzoylaminoquinolin-4-yloxy)-4-methylphenyl]-4-chloro-3-trifluoromethylbenzamide.

5. The aminoquinoline compound or pharmaceutically acceptable salt thereof according to claim 1, the pharmaceutically acceptable salt is a salt of an inorganic or organic acid selected from the group consisting of hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid, and toluenesulfonic acid.

6. A preparation method of a compound of Formula 1 or a pharmaceutically acceptable salt thereof according to claim 1, comprising:

(1) nitration of a compound of Formula 2 below so as to obtain a compound of Formula 3 below;

Formula 2:

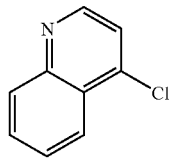

Formula 3:

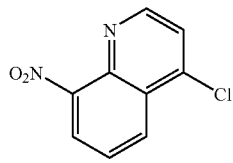

(2) substitution reaction of the compound of Formula 3 obtained in step (1) with an aminophenol so as to obtain a compound of Formula 4 below;

Formula 4:

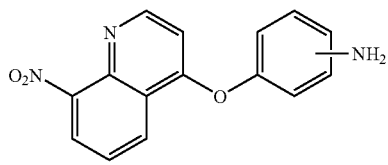

(3) coupling of the compound of Formula 4 obtained in step (2) with an isocyanate of a general formula $R^5$—NCO or a carboxylic acid of a general formula $R^5$—$CO_2H$, so as to obtain a compound of Formula 5 below;

Formula 5:

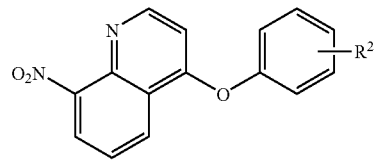

(4) reduction of the compound of Formula 5 obtained in step (3) so as to obtain a compound of Formula 6 below; and Formula 6:

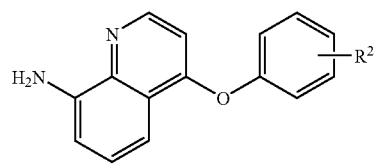

(5) amidation of the compound of Formula 6 obtained in step (4) with a carboxylic acid of a general formula $R^4$—$CO_2H$ so as to obtain the following compound of Formula 1.

Formula 1:

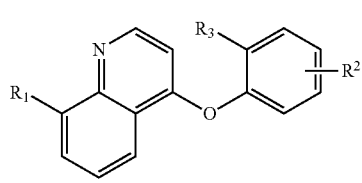

wherein $R^1$ is $NH_2$ or $NHCOR^4$;

$R^2$ is $NHCONHR^5$ or $NHCOR^5$;

$R^3$ is H;

$R^4$ is $C_1$-$C_6$ alkyl or $C_6$-$C_{10}$ aryl;

$R^5$ is $C_6$-$C_{10}$ aryl or $C_3$-$C_6$ heteroaryl which is unsubstituted or substituted with one or more substituents selected from the group consisting of $C_1$-$C_6$ alkyl; one or more halogen atoms selected from the group consisting of fluorine, chlorine, bromine and iodine; $C_1$-$C_6$ alkyl substituted with one or more halogen atoms selected from the group consisting of fluorine, chlorine, bromine and iodine; nitro; substituted or unsubstituted piperidinyl; substituted or unsubstituted imidazolyl; substituted or unsubstituted isoxazolyl; and substituted or unsubstituted morpholinyl, wherein the substituent on the piperidinyl, imidazolyl, isoxazolyl or morpholinyl is hydroxyl or $C_1$-$C_6$ alkyl.

7. A preparation method of a compound of Formula 1 or a pharmaceutically acceptable salt thereof according to claim 1, comprising:

(1) substitution reaction of a compound of Formula 3 below with a protected aminophenol so as to obtain a compound of Formula 7 below;

Formula 3:

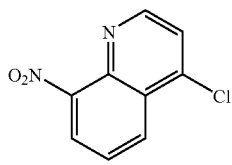

Formula 7:

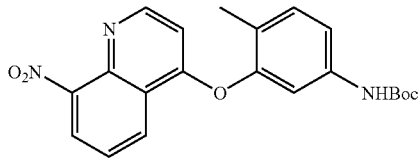

(2) reduction of the compound of Formula 7 obtained in step (1) so as to obtain a compound of Formula 8 below;

Formula 8:

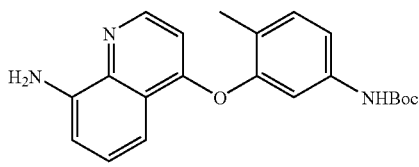

(3) amidation of the compound of Formula 8 obtained in step (2) with a carboxylic acid of a general formula $R^4$—$CO_2H$ so as to obtain a compound of Formula 9 below;

Formula 9:

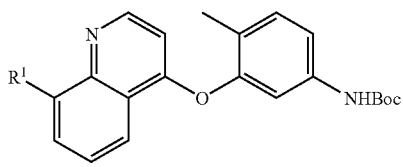

(4) deprotection of the compound of Formula 9 obtained in step (3) so as to obtain a compound of Formula 10 below; and Formula 10:

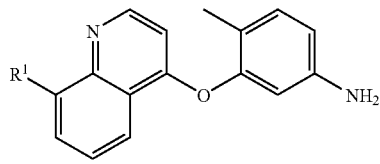

(5) coupling of the compound of Formula 10 obtained in step (4) with an isocyanate of a general formula $R^5$—NCO or a carboxylic acid of a general formula $R^5$—$CO_2H$, so as to obtain the compound of the following Formula 1:

Formula 1:

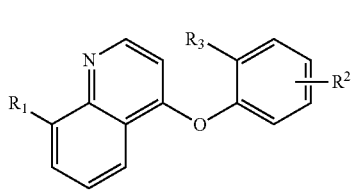

wherein
$R^1$ is $NH_2$ or $NHCOR^4$;
$R^2$ is $NHCONHR^5$ or $NHCOR^5$;
$R^3$ is $C_1$-$C_6$ alkyl;
$R^4$ is $C_1$-$C_6$ alkyl or $C_6$-$C_{10}$ aryl;
$R^5$ is $C_6$-$C_{10}$ aryl or $C_3$-$C_6$ heteroaryl which is unsubstituted or substituted with one or more substituents selected from the group consisting of $C_1$-$C_6$ alkyl; one or more halogen atoms selected from the group consisting of fluorine, chlorine, bromine and iodine; $C_1$-$C_6$ alkyl substituted with one or more halogen atoms selected from the group consisting of fluorine, chlorine, bromine and iodine; nitro; substituted or unsubstituted piperidinyl; substituted or unsubstituted imidazolyl; substituted or unsubstituted isoxazolyl; and substituted or unsubstituted morpholinyl, wherein the substituent on the piperidinyl, imidazolyl, isoxazolyl or morpholinyl is hydroxyl or $C_1$-$C_6$ alkyl.

8. A pharmaceutical composition for preventing or treating cutaneous cancer, comprising an aminoquinoline compound or a pharmaceutically acceptable salt thereof according to claim 1.

9. The pharmaceutical composition according to claim 8, wherein the aminoquinoline compound or pharmaceutically acceptable salt thereof inhibits proliferation of melanoma tumor cells.

10. The pharmaceutical composition according to claim 8, wherein the cutaneous cancer is basal cell carcinoma, squamous epithelial carcinoma or melanoma.

11. The pharmaceutical composition according to claim 8, comprising the compound of Formula 1 or pharmaceutically acceptable salt thereof in an amount of 0.5 to 10% by weight of the total weight of the composition.

12. The pharmaceutical composition according to claim 8, for administering the compound of Formula 1 or pharmaceutically acceptable salt thereof to a mammal in an amount of 0.001 to 100 mg/kg body weight per day.

13. The pharmaceutical composition according to claim 8, further comprising one or more diluents, lubricants or any combinations thereof.

14. The pharmaceutical composition according to claim 8, which is in the form of a formulation for oral administration selected from the group consisting of tablet, pill, hard or soft capsule, liquid, suspension, emulsion, syrup and granule.

15. The pharmaceutical composition according to claim 14, further comprising one or more components selected from the group consisting of a pharmaceutically acceptable bonding agent, a disintegrant, an effervescent mixture, an absorbent, a coloring agent, a flavoring agent, a stabilizer, a hydrating agent, an emulsifying accelerator, a salt for adjusting osmotic pressures and a buffer.

16. The pharmaceutical composition according to claim 8, which is in the form of a formulation for parenteral administration selected from an isotonic aqueous solution and a suspension.

17. The pharmaceutical composition according to claim 8, which is in the form of a sterilized formulation.

* * * * *